United States Patent
Liang et al.

(10) Patent No.: US 10,581,606 B2
(45) Date of Patent: Mar. 3, 2020

(54) SECURE SYSTEM FOR COUPLING WEARABLE DEVICES TO COMPUTERIZED DEVICES WITH DISPLAYS

(71) Applicant: THE TRUSTEES OF DARTMOUTH COLLEGE, Hanover, NH (US)

(72) Inventors: Xiaohui Liang, West Lebanon, NH (US); Tianlong Yun, Lebanon, NH (US); Ronald Peterson, Brattleboro, VT (US); David Kotz, Lyme, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 191 days.

(21) Appl. No.: 15/504,991

(22) PCT Filed: Aug. 18, 2015

(86) PCT No.: PCT/US2015/045651
§ 371 (c)(1),
(2) Date: Feb. 17, 2017

(87) PCT Pub. No.: WO2016/028752
PCT Pub. Date: Feb. 25, 2016

(65) Prior Publication Data
US 2017/0279612 A1 Sep. 28, 2017

Related U.S. Application Data (60) Provisional application No. 62/038,783, filed on Aug. 18, 2014.

(51) Int. Cl.
*H04W 12/08* (2009.01)
*G06F 21/35* (2013.01)
(Continued)

(52) U.S. Cl.
CPC .......... *H04L 9/3226* (2013.01); *A44C 5/0007* (2013.01); *A61B 5/0017* (2013.01);
(Continued)

(58) Field of Classification Search
CPC . H04W 4/00; H04M 1/6066; H04M 2207/18; H04L 2012/2841; H04L 9/085; H04H 20/71; H04H 60/23
See application file for complete search history.

(56) References Cited

U.S. PATENT DOCUMENTS 6,215,901 B1    4/2001  Schwartz
8,610,659 B2 *  12/2013 Fletcher ................ G06F 1/3203
                                                          345/102

(Continued)

FOREIGN PATENT DOCUMENTS

WO    WO 2013/096954 A1    6/2013

OTHER PUBLICATIONS

A Context-Aware User Interface for Wireless Personal-Area Network Assistive Environments. Paul et al. Wireless Pers Commun. (Year: 2013).*

(Continued)

*Primary Examiner* — Venkat Perungavoor
(74) *Attorney, Agent, or Firm* — Lathrop GPM LLP (57) ABSTRACT

A system has a first electronic device with optical sensor, digital radio transceiver, and processor with firmware; this device is typically portable or wearable. The system also has a computerized device with a display, a second digital radio transceiver, and a second processor with firmware. The first and computerized devices are configured to set up a digital radio link when in radio range. The second processor uses a spot on the display to optically transmit a digital message including a secret such as an encryption key or subkey and/or an authentication code adapted for authenticating an (Continued)

encrypting the radio link. The first device receives the digital message via its optical sensor, and uses the digital message to validate and establish encryption on the radio link. In embodiments, the system determines a location of the first device on the display and positions the transmission spot at the determined location.

20 Claims, 4 Drawing Sheets

(51) Int. Cl.
- H04L 9/32 (2006.01)
- G04G 21/04 (2013.01)
- A44C 5/00 (2006.01)
- A61B 5/00 (2006.01)
- G06F 3/14 (2006.01)
- H04L 9/06 (2006.01)
- H04L 9/14 (2006.01)
- H04L 9/30 (2006.01)
- G06F 21/43 (2013.01)

(52) U.S. Cl.
CPC ............ *G04G 21/04* (2013.01); *G06F 3/1454* (2013.01); *H04L 9/0618* (2013.01); *H04L 9/14* (2013.01); *H04L 9/30* (2013.01)

(56) References Cited

U.S. PATENT DOCUMENTS

| | | |
|---|---|---|
| 2009/0143689 A1 | 6/2009 | Berry et al. |
| 2011/0007328 A1 | 1/2011 | Wolf et al. |
| 2012/0317024 A1 | 12/2012 | Rahman et al. |
| 2013/0084069 A1 | 4/2013 | Feuer et al. |
| 2013/0159705 A1 | 6/2013 | Leedom |
| 2013/0234850 A1* | 9/2013 | Lee .................. A61B 5/02 340/539.12 |
| 2014/0044304 A1 | 2/2014 | Rhoads |
| 2014/0068744 A1 | 3/2014 | Bran et al. |
| 2014/0139486 A1* | 5/2014 | Mistry ............. G06F 3/0304 345/175 |

OTHER PUBLICATIONS

Device Connectivity Technologies Using Short-Distance Wireless Communications. Tamura et al. Fujistu Sci Tech J. (Year: 2013).*
Evidently secure device associations. Kinberg et al.HP invent Internal Publication. (Year: 2005).*
KR 100707364. Kim. (Year: 2006).*
WO 2017190776A. Paradells et al. (Year: 2017).*
IDcolor: A color based identification system. Miraz et al. (Year: 2011).*
International Search Report and Written Opinion of PCT/US2015/045651 dated Nov. 3, 2015, 11 pp.
International Preliminary Report on Patentability of PCT/US2015/045651 dated Feb. 21, 2017, 9 pp.

* cited by examiner

Table 1: Notation and LightTouch Bootstrapping Protocol

| | | | |
|---|---|---|---|
| $F$ | full-screen pattern | $\dashrightarrow_F$ | full-screen light source |
| $L$ | bracelet's location | $\dashrightarrow_L$ | light source at $L$ |
| $S$ | brightness samples | $\rightarrow, \leftarrow$ | RF channel |
| $g, a, b$ | Diffie-Hellman parameters | $C$ | secret challenge |
| $Enc, Dec$ | symmetric key encryption and decryption | $sk$ | session key |
| $h$ | secure hash function | $Cr$ | correlation algorithm |
| $L_b, t_b$ | bracelet's correlation parameters | $L_d, t_d$ | display's correlation parameters |

| | Display ($g_a = g^a$) | | Bracelet ($g_b = g^b$) |
|---|---|---|---|
| ① Localization | Send a full-screen pattern $F$ | $\dashrightarrow_F$ | Receive $S$ at one location $L$ |
| ② Calibration | Receive $S$, and derive location $L$ | $\leftarrow$ | Send $S$ |
| ③ Correlation | Send $H = h(g_a)$ and $C$ | $\dashrightarrow_L$ | Receive $H_b, C_b$ |
| | Send $g_a$ | $\rightarrow$ | Receive $g_a$ |
| | | | If $Cr(h(g_a), H_b, L_b, t_b) = 1$, $g_a$ is verified. Calculate $sk = h(g_a^b)$ |
| ④ Correlation | Receive $\mathcal{E}$ and $g_b$, and calculate $sk = h(g_b^a)$ If $Cr(C, Dec(sk, \mathcal{E}), L_d, t_d) = 1$, $g_b$ and connection is verified. | $\leftarrow$ | Send $\mathcal{E} = Enc(sk, C_b)$ and $g_b$ |
| | Send $\mathcal{D} = Enc(sk, \text{'success'})$ | $\rightarrow$ | If 'success' $= Dec(sk, \mathcal{D})$, connection is verified. |

SECURE SYSTEM FOR COUPLING WEARABLE DEVICES TO COMPUTERIZED DEVICES WITH DISPLAYS

RELATED APPLICATIONS

The present application is a 35 U.S.C. § 371 filing of International Application No. PCT/US2015/045651, filed Aug. 18, 2015, which claims priority to U.S. Provisional Patent Application 62/038,783 filed 18 Aug. 2014, each of which is incorporated herein by reference in its entirety.

GOVERNMENT INTEREST

This invention was made with government support under grant number CNS-1329686 awarded by the National Science Foundation. The Government has certain rights in the invention.

BACKGROUND

Small digital devices, including small portable wearable devices, including wearable medical devices, fitness bracelets, smart watches, and other forms of 'smart' jewelry, are increasingly popular to help users monitor their physical activities and receive notifications, but often have little space or battery power to spare for displays, keyboards, and other human interfaces. Other portable and wearable devices support applications relating to athletics, entertainment, shopping, photography, social communication, task reminders, home automation, warehouse or factory automation, personal navigation, and so forth. These portable and wearable devices can be wirelessly linked to larger electronic devices such as a personal smartphone, tablet, laptop, desktop computer, physician's or trainer's workstation, television, projector, monitor, or kiosk that have larger display subsystems and ample power, to permit use of the larger devices to display data recorded on the wearable devices. Such computerized devices are increasingly prevalent in homes, offices, schools, hospitals, hotels, fitness centers, airports and other public spaces. The goal of this invention is to make it easy for a person to securely connect her wearable device to a computerized device she encounters, for the purpose of viewing information from her device and possibly sharing that information with nearby acquaintances.

SUMMARY

A system has a first electronic device with an optical sensor, a first digital wireless radio transceiver, and a first processor coupled to a memory containing a firmware. The system also has a computerized device having a display subsystem, a second digital wireless radio transceiver, and a second processor. The second processor uses the display subsystem to transmit an optical digital message including at least one of an encryption subkey, an encryption key, and an authentication code adapted for authenticating a wireless radio link. The first device is configured to receive the digital message, and is configured to use the encryption subkey or authentication code of the optical message to establish an encrypted and verified wireless connection through the first digital wireless radio transceiver and the second digital wireless radio transceiver to the second processor.

In another embodiment, a method uses an intensity-modulated brightness channel to communicate a digital message from a computerized device to a wearable, or otherwise portable, electronic device. The computerized device includes a display subsystem, a second digital wireless radio transceiver, and a second processor coupled to a second memory, the display subsystem, and the second digital wireless radio transceiver. The portable electronic device includes an optical sensor, a first digital wireless radio transceiver, and a first processor coupled to a first memory, the optical sensor, and the digital wireless radio transceiver, the first memory containing a firmware. The method includes using the display subsystem of the computerized device and optical sensor of the wearable device to form an optical digital communication channel; sharing cryptographic information from the computerized device to the wearable device over the optical digital communication channel to allow the wearable device to verify cryptographic information sent by the computerized device over a digital radio communication channel to the wearable device; and establishing an encrypted communications session using the digital radio communication channel, in a manner that ensures the intended portable electronic device is securely connected to the intended computerized device.

DETAILED DESCRIPTION OF THE EMBODIMENTS

It is desirable to ensure that wearable devices only establish bidirectional links to, or "pair with", computerized devices when such links are desired, and further that they only establish links when authorized to do so. Further, in order to preserve privacy, it is desirable that such bidirectional links be encrypted to protect data from eavesdropping or tampering.

Such wearable devices may include GoogleWear smartwatches, the Nike FuelBand, the FitBit bracelet, pedometers and other activity logging devices including mileage recording devices usable with bicycles and activity recording devices adapted to receive information from, or to program, gym equipment. Other wearable devices include pulse or ECG monitors useful for detecting or monitoring cardiac arrhythmias, insulin pumps, glucose monitors, wearable medical record databases, computer access authorization devices, pagers and other message receivers, electronic watches, vehicle entry or vehicle engine-operation keys, pulse oximeters for detecting and monitoring sleep apnea patients, blood-pressure monitors, gaming interfaces, computer network rapid-login and authorization-level keys, and other devices. More broadly, this class of devices includes any wearable or small portable device with a wireless radio transceiver, limited in-built display capability (if any), typically no camera, no physical keypad or keyboard, and limited capacity battery power subsystems. For the purposes of this description, 'wearable' is meant broadly to include any portable electronic device that might be worn or carried by its user.

While wearable devices may be paired with smartphones, there are many occasions when a larger display and/or larger keyboard is desirable, or when display through an unpaired smartphone may be desirable.

The computerized devices may include smartphones, laptop or desktop computers, security access devices, restaurant tablet, library or internet-cafe computer, car dashboard display systems, exercise equipment, smart television devices, and projector devices—almost any system with a processor, display and a digital wireless radio transceiver.

We envision a new method by which a wearable can establish a secure connection to a computerized device, such as a television or computer monitor, based on the user's intention to connect to the computerized device. The user can then access and display the wearable device's information without having to carry any other personal devices.

One might imagine Near Field Communications (NFC) to be a suitable method to tackle this security problem due to its short working range. However, a recent study [nShield: a noninvasive NFC security system for mobile devices, by Ruogu Zhou and Guoliang Xing, MobiSys 2014, Pages 95-108; DOI 10.1145/2594368.2594376] shows that commodity NFC-enabled mobile devices can be eavesdropped from up to 240 cm away, which may compromise users' connection intentions and permit confusion particularly if a user wears two such devices or if multiple users are near the computerized device. Furthermore, until NFC is commonly installed in display devices, this approach requires hardware modifications.

Such connections must only be made intentionally so that information in the wearable device is protected from access or tampering by unauthorized third parties, must be secure to prevent impersonation attacks by other nearby devices, including other devices worn or carried by the same wearer, and must be easy to establish even when a new computerized device is encountered. We propose a secure wearable-to-computerized device connection solution. Our solution, named LightTouch, uses a brightness channel that is created between a low-cost, low-power, light sensor (the optical sensor) of a wearable device and the screen of the computerized device. In effect, the screen becomes an optical transmitter and the optical sensor becomes an optical receiver, forming a unidirectional "brightness channel" between the computerized device and the wearable device, a channel used to transfer a small secret that is used to bootstrap secure communication over a radio channel such as Bluetooth or Wi-Fi. A screen touch gesture is adopted by users to ensure the modulation of screen brightness can be accurately and securely captured by the ambient light sensor. Wireless coordination over the digital radio communication channel with the processor driving the computerized device establishes a shared secret key based on the brightness channel information, while preventing distant devices from observing the secret key; once the secret key is established the computerized device and the wearable device use that secret key to establish an encrypted digital radio wireless link over which data may be transmitted from the wearable device to the computerized device, some of which may be displayed or transmitted over a network to a server, and command, configuration, or other data may be transmitted from the computerized device to the wearable device.

Figure 1:
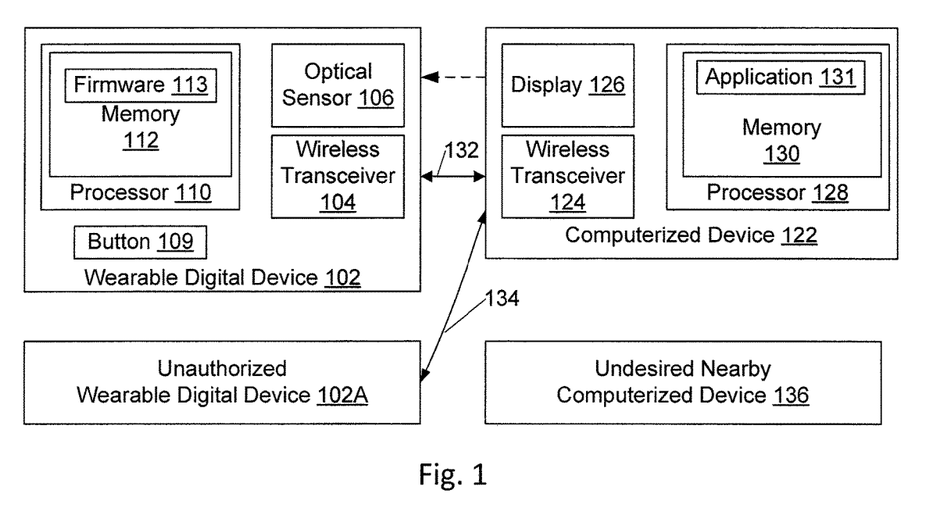
FIG. 1 is a block diagram of a basic embodiment of a system including a wearable device and a computerized device having a display.

A system has a first electronic device 102, the wearable device, with an optical sensor 106, a first digital wireless radio transceiver 104, and a first processor 110 coupled to a first memory 112 containing an encrypted communications link setup and communication firmware 113. In an embodiment the optical sensor is a photodiode or phototransistor. In an alternative embodiment the optical sensor is an electronic camera. The system also has a computerized device 122 having a display subsystem 126, a second digital wireless radio transceiver 124, and a second processor 128 with a memory 130 containing a LightTouch encrypted communications link setup and communication application 131.

The digital wireless transceivers 104, 124 are short-range digital radio transceivers configured with the ability to transmit digital information between the first and second electronic devices over an encrypted digital radio communications channel using an encryption process that is in some embodiments performed in the transceiver 104, 124, and in other embodiments is performed by executing encryption and decryption routines in the associated processors 110, 128; in the latter case, the encryption and decryption routines are part of firmware 113 and application 131. In a particular embodiment, the transceivers are capable of operation with Bluetooth frequencies and protocols, however many other short-range radio frequencies and protocols will function.

Figure 3:
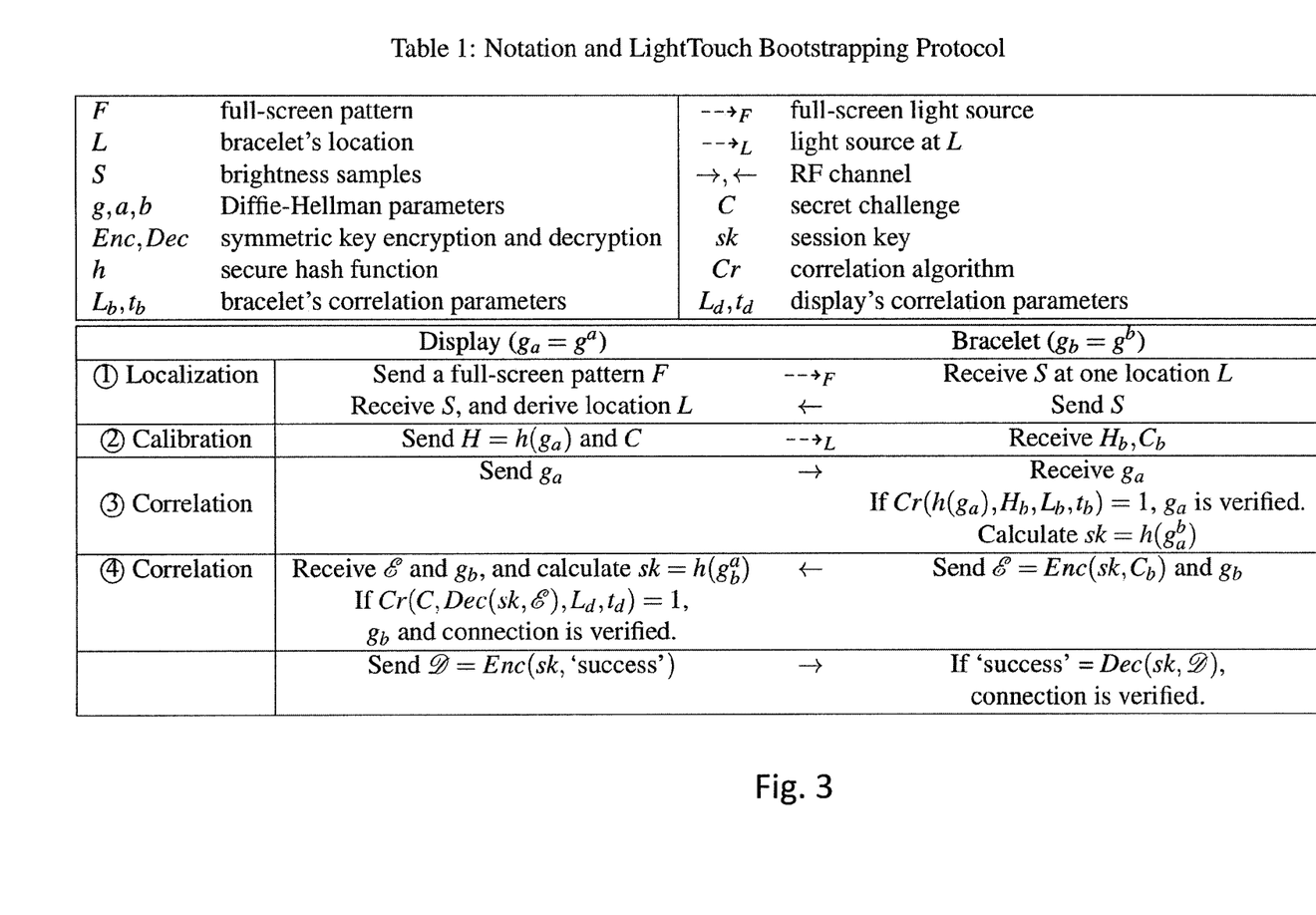
FIG. 3 illustrates handshaking used for establishment of an encrypted link between a wearable device and a computerized device.
Figure 4:
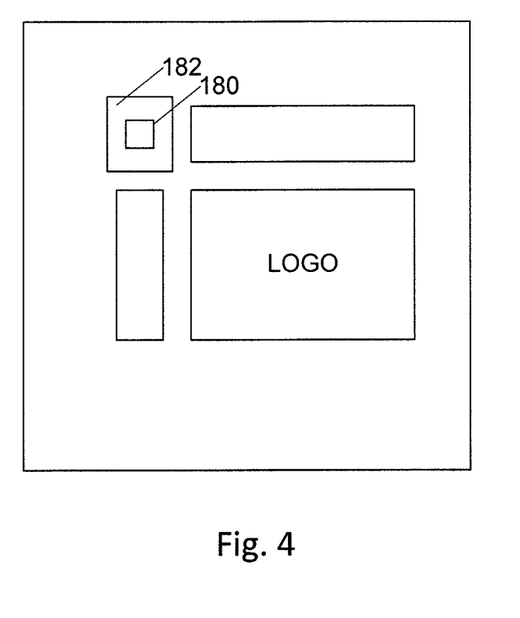
FIG. 4 illustrates a pattern on a screen of a display of a computerized device wherein a central data transmission spot is surrounded by a masking region.
Figure 5:
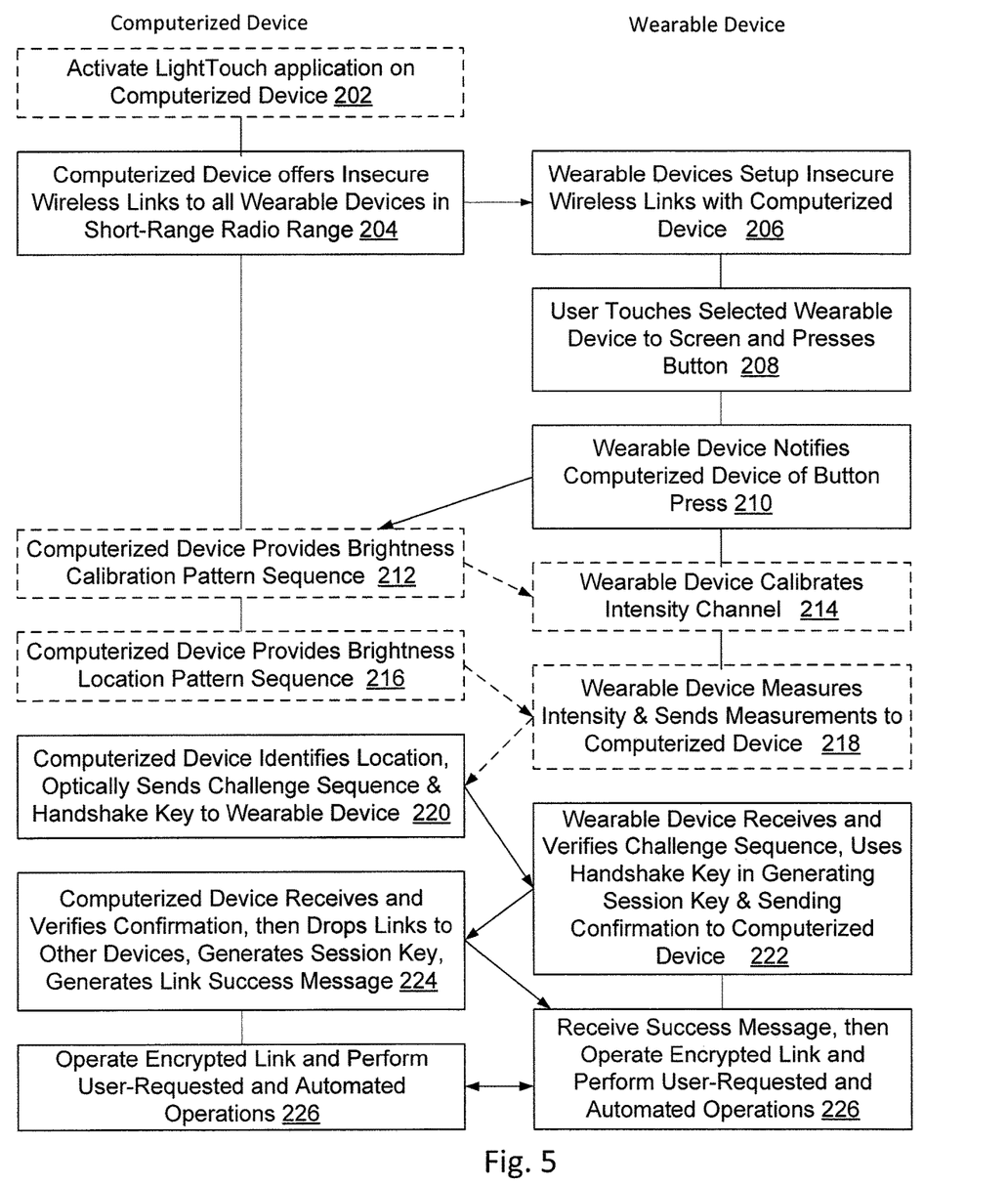
FIG. 5 is a flowchart of operation of the system of FIG. 1 when the LightTouch connectivity is activated.
Figure 6:
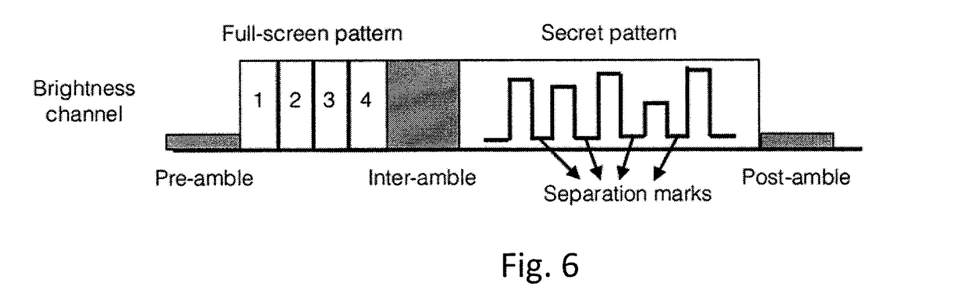
FIG. 6 is an approximate intensity-modulation waveform of a transmission spot on a display of the computerized device.

With reference to FIGS. 1-5, operation of the system begins with, for multipurpose computerized devices, wearer activation 202 of a LightTouch application 131 in memory 130 on the computerized device. We anticipate that some devices will be dedicated to use with LightTouch, so this step is illustrated in FIG. 5 as optional. The computerized device 122 offers 204 insecure short-range digital radio links 132, 134 to nearby wearable devices using transceiver 124, wearable devices in range respond 206 and set up digital radio communication with computerized device 204. In some systems, these short-range links are initiated upon a wearer pressing a button 109 on wearable device 102. The system then operates to convert a particular short-range digital radio link 132 to a secure encrypted link, while ignoring or even dropping other short-range digital radio links 134 to unauthorized or unintended devices 102A.

Once the links 132, 134 are set up, the computerized device awaits notification 210 of a button 109 press 208 over a particular digital radio link; this identifies a particular wearable device 102 and associated link 132 for potential conversion to a secure link.

A calibration procedure is then performed. Calibration may optionally be omitted on systems where the wearable device has been performed on systems where the particular wearable device and computerized device have been in communication recently with no changes to display settings, or where the wearer touches the wearable device to a designated communications icon 180 (FIG. 4) on the display 126 and localizing is unnecessary. In performing calibration, processor 128 displays 212 a sequence of calibration screens at several brightness levels, while notifying wearable device 214 of each calibration screen. Wearable device 102 observes light intensity as seen at optical sensor 106 and wearable processor 110 executing firmware 113 in its memory 112 determines a calibration therefrom.

Figure 2A:
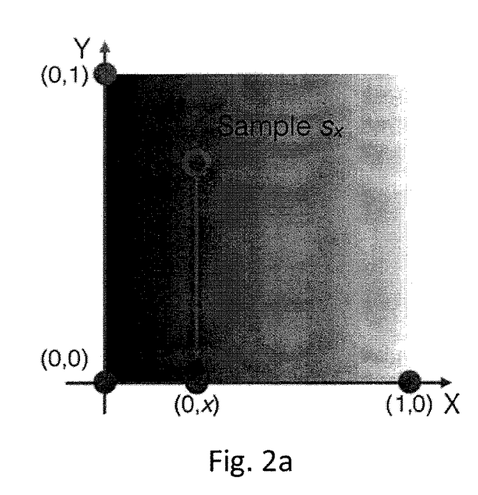
FIG. 2a and FIG. 2b illustrate successive screens used for localization of a wearable device that is being touched to a screen of a display of a computerized device.
Figure 2B:
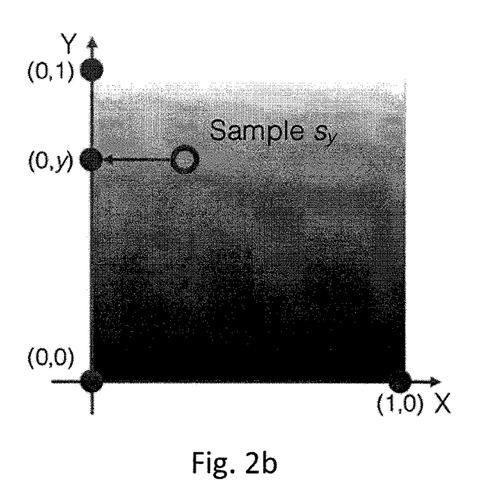

Next, in embodiments that do not require touching the wearable device at a designated communications icon on the display 126, the system localizes the wearable device by having processor 128 of the computerized device provide 216 on display 126 two or more localization patterns, which in an embodiment include X-gradient and Y-gradient localization patterns as illustrated in FIG. 2a and FIG. 2b respectively. Wearable device 102 observes these localization patterns with optical sensor 106 and transmits observed light intensity readings over digital radio link 132 to computerized device; the computerized device then determines a location on display 126 at which the sensor 106 of wearable device is located. In embodiments where the wearer is instructed to place the wearable device at a particular communications icon on display 126, the sensor 106 location is set to a location of the icon.

The second processor uses the display subsystem 126 to transmit 220 an optical channel message including at least an encryption session subkey, which may in some embodiments be a full encryption key, through the display 126, through brightness modulation of a data transmission spot on the display at the sensor 106 location on the display; in embodiments the data transmission spot is surrounded by masking patterns 182 to prevent other nearby devices from observing the data transmission spot. Once the session subkey is received 222 by the wearable device, this subkey is used in a handshake 222, 224, 226 that completes verification of computerized device identity, determination of full session keys, conversion of the unencrypted digital link 132 to an encrypted link, and initiation of additional automated and/or user-directed operations appropriate to the particular wearable device. In an embodiment, the transmission spot has a diameter of 5 centimeters or less to minimize risk of interception of the optical channel message by other devices.

In an embodiment having an 8-bit intensity capability, the optical channel message is encoded with 5 binary bits in 32 discrete intensity levels. In another embodiment, 37 discrete intensity levels are used to encode each symbol; in a particular embodiment where 25 symbols are displayed each second, a message having the equivalent of 130 bits may be transmitted in one second.

In alternative embodiments, 3 or 4 binary bits are encoded in 8 or 16 intensity levels respectively. In embodiments, symbol rates of 10, 15, 20, 30, 40, or 50 symbols per second are transmitted through the optical channel; the symbol rate is chosen to be compatible with a frame refresh rate of the display 126, such that each symbol is allocated an integer number of refreshed frames.

In a particular embodiment, in handshaking 222, 224, 226 to validate computerized device identity and conversion to an encrypted link, the first or wearable device receives part or all of a public key, or a hash of the public key, from the computerized device using its optical sensor 106, and verifies the public key received optically matches a key received over its short-range digital radio wireless transceiver 104 to verify the computerized device it is attempting to connect with through the digital radio transceiver is the same device as intended by the user. Session keys or subkeys are then exchanged to establish an encrypted wireless connection through its digital wireless transceiver 104 and the second digital wireless transceiver 124 to the second processor 128.

In another embodiment, as illustrated in FIG. 3, an initial wireless link is established between computerized device 122 and first device 102; other, unauthorized (or unintended) devices 102A may also establish initial wireless links to computerized device 122; these initial wireless links are encrypted with a public-key encryption using a public key P provided by the computerized device. In embodiments permitting placement of the first device anywhere on the screen, the computerized device sends a sequence of location identifying images through its display; these are received by the first device through its optical sensor and the first device transmits its location to the computerized device. To verify which device 102, 102A is to be authorized, the computerized device then sends a hash value H derived from its public key P, and a challenge code C, through intensity-modulation of a transmission spot on display 126 to wearable device 102. In an embodiment, the hash value H is a hash of its Diffie-Hellman (DH) public parameter $g_a$ (that is, $H=h(g_a)$ for a suitable well-known one-way hash function $h(\ )$) and challenge code C is a freshly chosen challenge C. It runs an encoding algorithm to convert (H; C) into a brightness pattern.

In an embodiment, the transmission spot is in a circular screen area centered at location L with a radius r. If the wearable device is held at an actual on-screen location L' within distance r of L, it receives a sequence of brightness values corresponding to the pattern. After a calibration algorithm (separating the values and eliminating the redundant values), the wearable device obtains a sequence of calibrated brightness values ($H_b$; $C_b$); these values should be correlated to (H; C) due to our encoding and calibration algorithms, but may not be identical due to factors like environmental noise, device motion, or physical inaccuracies in the screen or optical sensor.

The display sends its DH public parameter $g_a$ to the wearable device via the radio channel. If the wearable device connects to the target display, it receives the correct $g_a$ and obtains $H=h(g_a)$. The wearable device then runs a correlation algorithm to calculate the correlation score between H and $H_b$. Assuming the authenticity of the brightness channel, the wearable device believes $H_b$ is from the target device and accepts H to continue connection process if the correlation algorithm confirms the display 126 is indeed associated with the device it is in digital radio communications with, and not another device 136. The wearable device computes the session key sk=$h(g_a^b)$ upon its secret b and the public key of the display $g_a$.

The wearable device encrypts challenge code $C_b$ with session key sk to obtain ciphertext E=Enc(sk; $C_b$), where Enc( ) is the function that encrypts its second argument using a key provided as its first argument. The wearable device sends the ciphertext E and its own DH parameter $g_b$ to the display over the radio channel.

Only the display knowing secret a can calculate the session key sk=$h(g_b^a)$ and obtain $C_b$=Dec(sk; E) where Dec( ) is the function that decrypts its second argument using a key provided as its first argument. If the display finds that $C_b$ is correlated to C, it confirms the connection; otherwise, it stops the protocol. The intuition is that C can only be received by the target wearable device (assuming the secrecy of the brightness channel), and therefore, receiving a sufficiently-correlated $C_b$ means the display is indeed connected to the target wearable device.

The wireless radio transceivers 104, 124 are compatible with existing wireless standards such as 802.11 "Wi-Fi", Bluetooth, or similar moderate- to short-range digital radio communication systems. Once the wearable device is securely connected to the intended computerized device, the wearable device can use this secure radio communications channel for transmitting information to the computerized device for presentation on its display.

A verified session is established when the photosensor data matches (correlates to) expected data to within limits, thereby verifying that a user has placed the wearable device on a particular optically-transmitting location of the display 126, or near enough to that location that the optical sensor 106 can detect intensity modulations of the optically-transmitting location of the display. The optically-transmitting location of the display, together with the optical sensor, form a physically authenticated out-of-band channel that is hidden from other nearby devices by a combination the wearable device and the user's hand and by illuminating other portions of a screen with masking patterns.

It is anticipated that the optical sensor may double as an ambient-light sensor, already common equipment in activity monitor devices similar to FuelBand, MotoActv, or MetaWatch.

The above-described method allows a wearable device, requiring only a simple ambient-light sensor, to connect to a large display device through a wireless (radio) communications channel, by leveraging the brightness channel to discern the wearer's intent and to bootstrap the secure exchange of a session key on the wireless radio channel.

This method is superior to alternative approaches that require a camera on the wearable device (such as those that photograph a code on the display), that require an additional radio channel to be supported by both devices (such as near-field communication, NFC), or that require a keyboard or keypad on either device (as might be used to enter a numeric code displayed by the other device).

How do Target Computerized Devices Know when to be Active?

Devices are in sleeping mode if no one uses them. The user must have some way to activate the desired display device, and her wearable device, when a connection is desired. One simple approach is for the user to press a button on each, but our solution is system is agnostic to this initiation step and other approaches are possible. For example, proximity sensors of one device may detect another device is approaching, and then awake the devices. A discovery protocol is then initialized by one device, and a connection request is then sent to wake up available displays and have them display a touch-spot in the communication range. In this phase, multiple devices may change their status from sleeping to active to initiate or accept connection requests.

How do Target Devices Create Secure Communication?

Multiple devices might be active within short-range digital radio range because multiple users express their intent simultaneously, or multiple devices are brought within range of a single computerized device. The wearable device and computerized device need to quickly find and create a secure communication with each other.

Our LightTouch solution uses a one-way brightness channel as an out-of-band channel between the wearable and computerized devices to share a secret and bootstrap secure radio communication.

To enhance bandwidth of (typically slow) display devices, and to render it difficult for nearby devices to pick up the secret key or subkey, an intensity modulated link capable of transmitting multiple bits per intensity interval is used as described below.

Connection Algorithm

A user places a wearable device in contact with a display of the computerized device. (The computerized device need not be sensitive to touch.)

In the first step, the computerized device runs a localization algorithm to quickly derive the on-screen location L of the wearable device. The computerized device uses the display to send a full-screen pattern F. If the wearable device is held at any on-screen location of the display, it receives a brightness sample S. The wearable device returns S to the computerized device via the radio channel, and the computerized device then derives the location L based on F and S. A sequence of full-screen patterns may be used.

In the second step, the computerized device sends a hash value H of its public key P and a freshly chosen challenge C to the wearable device. It runs an encoding algorithm to convert (H; C) into a secret pattern. The computerized device shows the secret pattern in a circular screen area centered at L with a radius r. If the wearable device is held at an actual on-screen location L' within radius r of L, it receives a sequence of brightness values corresponding to the secret pattern. After a calibration algorithm (separating the values and eliminating the redundant values), the wearable device obtains a sequence of calibrated brightness values ($H_b$; $C_b$), which should be correlated to (H; C). Note that, C as a secret challenge will not be repeatedly used by the display. The use of a hash value H instead of the full public key P is to reduce the communication overhead because the brightness channel has much smaller data transmission rate than the radio channel.

In the third step, the computerized device sends its public key P to the wearable device via the radio channel. If the wearable device connects to the target computerized device, it receives the correct P and computes hash H=h(P). The wearable device then runs a correlation algorithm to calculate the correlation score between H and $H_b$. The correlation algorithm takes inputs of (H; $H_b$; $L_b$; $t_b$) and outputs true if the correlation score is less than a predefined threshold $L_b$ and the difference of H and $H_b$'s lengths is less than $t_b$, and outputs false otherwise. Due to the authenticity of the brightness channel, the wearable device trusts $H_b$ is from the target device and only accepts H if the correlation algorithm outputs true. The intuition of using thresholds $L_b$ and $t_b$ is to tolerate some noise in the brightness channel.

If the wearable device accepts H, it proceeds to the next step; otherwise, it stops the protocol.

In the fourth step, the wearable device encrypts $C_b$ with session key sk and sends the ciphertext E and $g_b$ to the computerized device. Only the computerized device knowing secret a can calculate the session key sk=h($g_b{}^a$) and obtains $C_b$=Dec(sk, E). If the computerized device finds that $C_b$ is correlated to C, it then proceeds to the data communication phase; otherwise, it stops the protocol. The intuition is that C can only be received by the target wearable device due to the secrecy of the brightness channel, and therefore, receiving a sufficiently-correlated $C_b$ means the computerized device is connected to the target wearable device.

The correlation algorithm in this step has inputs (C; $C_b$; $L_d$; $t_d$) where $L_d$ and $t_d$ are thresholds used for tolerating noise in the channel, which are set in the display.

After finishing the four steps in the bootstrapping phase, both devices now have the session key sk, unknown to other devices, and use sk to securely transmit the data via the radio channel in the data communication phase. The secure connection is successfully created.

The effectiveness of this solution, both its security and its ease of use, depends on the effectiveness of the out-of-band channel. However, we found the brightness channel is easily impacted by many unknown factors, such as the screen type, the ambient light sensor, the brightness and contrast settings of the screen, the ambient light condition, and the wrist motion. Most LCD monitors support low screen refresh frequency (60-75 Hz), and the ambient light sensor may respond slowly to sudden changes in screen brightness. In addition, the bootstrapping phase needs to be finished in seconds for usability. All these facts and requirements make it difficult to have a high throughput of the brightness channel. In the following, we propose the details of our algorithms where unique and novel properties of the wearable device and computerized device scenario help to overcome these challenges.

B. Localization Algorithm

We design a full-screen pattern F, which is shown on the full screen. The wearable device placed at any on-screen location is able to capture a sample of F. F is a sequence of four distinctive full-screen images Fmin; Fmax; Fx; Fy, where Fmin is filled with a gray scale (Tmin; Tmin; Tmin), Fmax is filled with a gray scale (Tmax; Tmax; Tmax), Fx is filled with fine-grained gray scales (T; T; T) where pixel brightness T increases monotonically from Tmin to Tmax along the X-axis as shown in FIG. 2A and Fy is filled with the same gray scales, which increase monotonically along the Y-axis as shown in FIG. 2b. The wearable device is supposed to receive four readings S=(smin; smax; sx; sy) corresponding to four images respectively, and send S back to the computerized device via the radio channel in the sequence they were received. The computerized device receives S, calculates the derived location L=(x; y) based on F and S, and shows the secret pattern in a circular screen area centered at L with a radius r. The computerized device sets r to an appropriate value, chosen to be not too small (so the wearable device can receive the secret pattern) and not too large (to ensure the wearable device and user's body parts can cover and protect the light source and restrict observation by others nearby).

In alternative embodiments, a designated touch-spot icon is shown on a screen of a computerized device, and connection begins when the wearable device is touched to the touch-spot.

Alternative Localization

The localization algorithm helps the display to calculate a derived wearable device location L', which could be different from its actual location L. In practice, the display is not able to obtain L or D=‖L−L'‖. As such, the computerized device has to choose a radius r large enough to ensure the optical sensor can access the light source regardless of D. We tested the full-screen pattern by using a window having 1920 by 1080 pixels on a monitor having screen area 44.8 by 25.2 cm, and a window having 800 by 800 pixels on a monitor having screen area of 21.5 by 21.5 cm.

Since the localization accuracy is important to the security goals of LightTouch, we improved the localization accuracy by using the following methods. The first two methods are variants of the "linear method" described above.

1) Multi-time method: If the display shows the full-screen pattern multiple times, the optical sensor will capture multiple samples. The computerized device checks the average values of the samples and derives a more precise location with averaging. The Multiple-time method generally outperforms the one-time localization algorithm by reducing the necessary r by 0.23-0.61 cm. An obvious disadvantage of this method is that it increases the duration of use of the brightness channel.

2) Two-stage method: The idea for this method is to adaptively change the size of the screen pattern in two stages. In the first stage, the display shows the full-screen pattern at full size, in a particular experiment 1920 by 1080 pixels. Suppose the display obtains a derived location L' and based on the linear method it knows the maximum localization error is $r_1$. In the second stage, the display shows a smaller pattern centered at L' with a smaller size ($2r_i$; $2r_1$). This guarantees the smaller pattern can be seen by the optical sensor. After receiving the second sample corresponding to the smaller pattern, the display derives a more precise location of the wearable device.

The two-stage method significantly improves the localization accuracy compared to the one-time and the multi-time linear methods. With the two-stage method, r can be chosen around 1 cm or even less than 1 cm in some cases, easily meeting the goal (r less than 5 cm) required for the wearable device and user's hands to block an attacker's view of the optical message transmission spot. The two stage method only doubles the time duration of using the brightness channel and keeps the features of the linear interpolation, which is easily generalized.

Non-Linear Method:

Readings from optical sensors do not have a strictly-linear relation with gray scale for many reasons, and many displays operate with an assumed Gamma correction. In our experiments the light captured by the photocell from the screen has been altered by a Gamma correction in the display subsystem. So we tried learning what the error is in sensor readings for different gray scale values and using that learned error to reverse the effects of Gamma correction. We ran tests of localization and based on the measured error D we learned a reverse Gamma correction function the inverse Gamma correction as the last step of localization, creating a non-linear localization method.

We have therefore demonstrated methods to localize contact of a wearable device to a display of a computerized device to an accuracy of as little as 2 percent of screen dimensions.

C. Encoding Algorithm

The computerized device runs an encoding algorithm to convert a number into a secret pattern. A secret pattern is a sequence of gray scales. The number of used gray scales is a constant k, which is known to both the computerized device and the wearable device.

The gray scales (from the most dark to the most bright) are denoted by $b_1$, $b_k$ where $b_1$=(Tmin; Tmin; Tmin) and $b_k$=(Tmax; Tmax; Tmax). To encode H, the computerized device converts H into a β-length k-ary number h1 . . . hβ where hj∈|0,k−1| for 1<j<13.

The computerized device then finds the gray scale $b_{hj}$ and maps H to ($b_{h1+1}$, . . . $b_{hβ+1}$).

D. Calibration Algorithm

The wearable device and computerized device adopt a specially-designed calibration algorithm. The computerized device adds recognizable signals to the pattern, and the wearable device can extract the pattern from the sensor readings by using these signals. Calibration is an important step to convert a sequence of noisy sensor readings into a readable pattern. As shown in FIG. 4, the preamble, interamble, and postamble are signals added to help the wearable device to detect when and what patterns are transmitted.

The preamble is used to indicate that the full-screen pattern is about to send, and the postamble is used to indicate that the whole transmission is ended. The interamble is used to indicate that the localization is finished and the secret pattern is about to be sent. The pre/postamble are set as black, while the inter-amble is set as white. All three are displayed for a relatively long time period $T_a$ to be recognizable for the wearable device.

Assume the computerized device shows the secret pattern at frequency $1/T_b$, i.e., each gray scale is shown for period $T_b$. LightTouch requires the receiving frequency at the ambient light sensor to be higher than $1/T_b$ such that each gray scale has at least one sensor reading. However, a higher receiving frequency may cause repeated sensor readings for one gray scale symbol.

LightTouch uses separation marks to ensure the sensor is synchronized to grayscale symbols transmitted on the optical channel. Each separation mark is added between any two gray scales in the full-screen pattern and the secret pattern as shown in FIG. 3. The separation mark is set as black with time period $T_f$ shorter than $T_a$ so it is distinguishable from the minimum gray scale Tmin and pre/inter/poster-amble; this is a return-to-zero (RZ) symbol encoding. In an alternative embodiment, separation marks are omitted, resulting in an NRZ (no-return-to-zero) encoding.

Adding separation marks enables the wearable device to separate the sensor readings for different gray scales. For each gray scale, the wearable device receives a group of sensor readings. Since most ambient light sensors are basically resistors, they do not respond instantly to changes in screen brightness. The computerized device may also have a performance delay of showing the patterns. Finally, the display and the wearable device synchronize time using the separation marks. The wearable device considers the series of sensor readings, one window W at a time. We set the window width to match the signal period, $T_b+T_f$. If the number of readings during $T_f$ is $N_f$, and the number of readings during $T_b$ is $N_b$, the window has $N=N_f N_b$ readings. The wearable device finds the maximum reading within the N-reading window; if the middle value of the peak-detection window is the peak value, W is shifted forward by $\lfloor N/2 \rfloor$, i.e., the $\lfloor N/2 \rfloor$ oldest values in the window are replaced with $\lfloor N/2 \rfloor$ newest ones; if not, W is shifted by 1, i.e., the oldest value in the window is replaced with the new one. In this way, the grayscale value is extracted (the peak value in the window) and the window quickly becomes aligned with the signal. The length N is set so that $\lfloor N/2 \rfloor <= N_f$ to capture the peak value if it appears at the end of $T_b$, and $\lfloor N/2 \rfloor >= N_b$ to avoid capture of two repeated peak values for one grayscale value. As such, we have $N_b <= \lfloor N/2 \rfloor <= N_f$. If the sensor uses a constant frequency, we have $T_f >= T_b$. To improve the efficiency, we choose the minimum $T_f = T_b$.

The separation marks and the peak-detection are also used for transmitting and receiving the full-screen pattern. Since the localization accuracy determines the effectiveness and the security of LightTouch, we prefer to choose larger $T'_b$ and $T'_f$ for showing the full-screen pattern than $T_b$ and $T_f$. The total time duration we use the brightness channel in LightTouch is thus $T=3T_a+8T'_b+T'_f+2(2\beta-1)T_b$.

E. Correlation Algorithm

For LightTouch, we prefer a fault-tolerant correlation rather than a decoding algorithm for two reasons: i) the sensor readings are not always accurate enough for decoding because the screen and the ambient light sensor may have performance delay while transmission time needs to be short for usability; and ii) the wearable device and the computerized device have a common high-bandwidth radio channel that can be leveraged. The wearable device receives a sequence of brightness values from the computerized device, and obtains $H_b$ after calibration. It also obtains P from the computerized device via the radio channel and calculates $H=h(P)$. $(L_b; t_b)$ are adjustable parameters. The correlation algorithm, with inputs $(H; H_b; L_b; t_b)$, determines if the correlation score of H and $H_b$ is less than $L_b$ and the difference of their lengths is less than $t_b$, and outputs false otherwise. We denote $H_b$ after normalization by $H^-_b$ and H after normalization by $H^-$. H and $H_b$ might not be of equal length. We use a dynamic time warping algorithm to calculate the correlation score of $H^-_b$ and $H^-$.

If we choose a larger $L_b$ or $t_b$, the wearable device tolerates more differences between $H_b$ and H (high usability), and the chance for the impersonation attacks to succeed is greater (low security). The correlation algorithm is also used by the computerized device to check C and $C_b$ in a similar way. After the wearable device sends $C_b$ to the computerized device, the computerized device uses a similar correlation with parameters (Ld; $t_d$) to verify that C and $C_b$ are correlated. Together, these two correlation procedures help balance the usability and security of the system.

Security Discussion

We consider four attacks:

(A1) impersonation attacks of the target computerized device, (A2) impersonation attacks of the target wearable device, (A3) eavesdropping attacks, and (A4) modification attacks of data transmitted over the radio channel.

Note that, if the attacker launches a man-in-the-middle (MITM) attack over the radio channel to impersonate both devices, it could obtain the radio packets without being detected. However, since LightTouch helps two devices develop a secret session key, attacker A3 cannot decrypt the radio packets and attacker A4 cannot modify the radio packets without being detected. The session key is secret unless the attacker succeeds as MITM, that is, achieving both A1 and A2 attacks. We thus analyze attacks A1 and A2 here, and evaluate their likelihood of success.

Impersonate Target Computerized Device [A1]

Consider an impersonation attacker A1 that connects to the target wearable device over the radio channel. If A1 aims to impersonate the target computerized device to successfully share a session key with the target wearable device, it has to ensure the wearable device successfully finishes the LightTouch protocol steps. The difficulty of doing so for A1 is that the brightness channel is created between the target computerized device and the target wearable, and that channel is not controlled by A1. To make the wearable believe that the current connection is correct, A1 has to make the target computerized device show the brightness pattern at the wearable's on-screen location. Otherwise, the wearable quits the protocol because no brightness pattern is received. To do so, A1 needs to use another device and connect the device to the target computerized device. A1's device generates four fake samples in the localization algorithm so that the computerized device shows the pattern under the target wearable. The pattern includes a number $H=h(g_a)$ where $g_a$ is the Diffie-Hellman (DH) public parameter of the computerized device. $g_a$ and H are considered to be known to A1 because $g_a$ is sent through the radio channel to A1's device. $H_b$ is the value received at the target wearable device through the brightness channel. $H_b$ is correlated to H, but $H_b$ contains errors due to varying performance of the display and sensor. LightTouch allows the wearable device to tolerate the difference between the hash value received from radio channel and $H_b$. As such, $H_b$ is even more important than H, since if $H_b$ is obtained by A1, A1 can pre-check if the hash of a forged public key matches $H_b$ and increase its success probability. However, A1 is unable to obtain $H_b$.

The proposed localization algorithm contributes to security by preventing A1 from receiving the pattern sent over the brightness channel. A1 cannot obtain any useful information about $H_b$ from the bootstrapping phase.

Now, let us check the bootstrapping protocol; if A1 uses $g_a$, it could pass the check but it is not be able to obtain $sk=g_b^a$ without knowing a or b; otherwise, A1 generates $g'_a$ and hopes $H'=h(g'_a)$ correlates with $H_b$. H is the only information that A1 could use in evaluating H'. Our experiment results show that A1 fails in generating such H' with a very high probability.

Light Injection to Brightness Channel.

Imagine A1 tries to inject light information to the brightness channel between the computerized device and the wearable device. Since the light sensor is tightly touched to the screen and the screen is bigger than the wearable device, the screen portion underneath the wearable device is the only light source that impacts the sensor readings, and A1 has no capability to inject light into the brightness channel. A1 can also try to inject light information when the user does not hold the wearable device towards the screen. But in this case, the user has no intention of initiating connections and the wearable device won't be activated (recall that we assume A1 has no physical access to the wearable device).

Impersonate Target Wearable Device [A2]

Consider an impersonation attacker A2, which has a device that connects to the target computerized device and A2 aims to impersonate the target wearable device and share a session key with the target computerized device. During the localization algorithm, A2's device sends four fake samples to the computerized device. The computerized device then shows the brightness pattern at a location, which could be the target wearable device's on-screen location or a different location. If the pattern is shown at the target wearable device's onscreen location L, the proposed localization algorithm helps achieve the secrecy of the brightness channel. That means A2 is unable to obtain the pattern, which contains the secret challenge $C_b$.

The target wearable device sends $g_b$ and a ciphertext $D=Enc(sk; C_b)$, wherein $C_b$ is encrypted by key sk to produce ciphertext D, to the computerized device via radio channel in the bootstrapping protocol. If A2 wants to obtain $C_b$, it needs to know the corresponding $sk=g^a{}_b$. If A2 wants to obtain $sk=g^a{}_b$, A2 has to obtain a, which means A2 must successfully launch the impersonation attacks of target computerized device (A1), which is difficult as shown above. Without receiving any information about C and $C_b$, it is very difficult for A2 to forge a $C'_b$ that is correlated with the original secret challenge C. If the pattern is shown at a different location other than L, A2 could obtain the pattern $C_b$, and should able to connect with the target computerized device. This is unpreventable because A2 and the target wearable device are no different from the display's perspective. The localization enables the target wearable device to quickly detect such attacks: the wearable device receives no pattern through the brightness channel after localization and alerts its wearer of a failed connection. Note that, since the secret challenge C and the DH public parameter $g_a$ are set for one-time use, A2 does not gain any advantage by obtaining $C_b$ and $g_a$ from previous transactions.

Prototyping and Evaluation

Security, compatibility, and usability are three goals for LightTouch. For compatibility, we first implemented the LightTouch wearable device using a popular Arduino board equipped with an ambient light sensor (photocell) and a Bluetooth Low Energy (BLE) module; we implemented the LightTouch computerized device as a Python program compatible with MacOS, Windows, and Linux operating systems. The radio channel between the wearable device and the display is implemented using Bluetooth Low Energy (BLE), which is widely supported by existing bracelets, smartphones, tablets, laptops, and computers due to its low power consumption. To evaluate usability, we tested LightTouch for three photocells and two displays (an HP monitor and an iMac). LightTouch achieved an average 98% successful connection ratio while resisting impersonation attacks against the computerized device and the wearable device, an encouraging result.

For purposes of this document, a subkey is information that forms either the full key required for encryption or decryption of information transmitted over an encrypted digital link, or a portion, including multiple bits, that when combined with other information forms the full key required for encryption or decryption.

For the purposes of this document, phrases like radio channel, digital radio wireless link, digital radio link, radio communications channel, wireless link, wireless channel, and wireless communication channel, are all intended to refer to the digital radio communication channel formed between two or more digital wireless radio transceivers. Bluetooth, and Bluetooth Low Energy, Wi-Fi, and wireless networks based on the IEEE 802.11 standards, are all common technologies that usable to form a digital wireless radio communication channel, but other protocols and standards may be used and the inventions described herein are not limited to those specific technologies.

Similarly, for the purposes of this document, phrases like wireless transceiver, digital wireless transceiver, digital radio transceiver, and radio transceiver, are all intended to refer to a digital wireless radio transceiver suitable for forming the digital radio communication channel.

Combinations of Features

The system and method herein described may be implemented with several combinations of features. Among those combinations are:

A system designated A including a first electronic device that has an optical sensor, a first digital wireless radio transceiver, and a first processor coupled to a first memory, the optical sensor, and the digital wireless radio transceiver, the first memory containing a firmware, and a computerized device that has a display subsystem, a second digital wireless radio transceiver, and a second processor coupled to a second memory, the display subsystem, and the second digital wireless radio transceiver, the second memory containing an optical communications application. The optical communications application includes machine-readable instructions configured to present a digital message as a sequence of symbols, each symbol encoded as an optical intensity, at a transmission spot on a screen of the display subsystem; and the firmware has machine-readable instructions for receiving the digital message through the optical sensor, the digital message comprising at least one of an encryption subkey and an authentication code adapted for authenticating a wireless connection between the first electronic device and the computerized device, and to use the digital message to establish an encrypted wireless connection from the first processor through the first digital wireless radio transceiver and the second digital wireless radio transceiver to the second processor.

A system designated AA including the system designated A wherein the digital message is encoded with at least 3 bits per symbol.

A system designated AB including the system designated A or AA wherein the intensity of the transmission spot returns to black between symbols while transmitting the digital message.

A system designated AC including the system designated A, AA, or AB, wherein the optical communications application further comprises machine-readable instructions to locate a position of the optical sensor on the display, and wherein the transmission spot is centered upon the located position.

A system designated AD including the system designated A, AA, AB, or AC wherein the transmission spot is sized smaller than 5 centimeters diameter.

A system designated ADA including the system designated AD wherein the display has a screen size exceeding 16 centimeters in at least one axis.

A system designated ADB including the system designated AD wherein the display has a screen size exceeding 40 centimeters in at least one axis.

A system designated AE including the system designated A, AA, AB, AC, AD, ADA or ADB wherein the firmware comprises machine-readable instructions for performing a correlation to ensure accurate transmission of the optical digital message.

A system designated AF including the system designated A, AA, AB, AC, AD, AE, ADA, or ADB wherein the optical digital message comprises a public key of a cipher.

A method designated B of using an intensity-modulated brightness channel to communicate a digital message from a computerized device to a wearable electronic device, where the computerized device includes a display subsystem, a second digital wireless radio transceiver, and a second processor coupled to a second memory, the display subsystem, and the second digital wireless transceiver. The portable electronic device includes an optical sensor, a first digital wireless radio transceiver, and a first processor coupled to a first memory, the optical sensor, and the first digital wireless radio transceiver, the first memory containing a firmware. The method includes using the display subsystem of the computerized device and optical sensor of the wearable device to form an optical digital channel; sending cryptographic information from the computerized device to the wearable device over the optical digital channel to allow the wearable device to verify cryptographic information sent by the computerized device over a radio channel between the first and second wireless radio transceivers to the wearable device and to adopt a session key; and establishing an encrypted communications session using the radio channel and session key, in a manner that ensures the intended portable electronic device is connected to the intended computerized device.

A method designated BA including the method designated B wherein the digital message is encoded with at least 3 bits per symbol.

A method designated BB including the method designated B or BA wherein the intensity of the transmission spot returns to zero between symbols while transmitting the digital message.

A method designated BC including the method designated B, BA, or BB wherein the optical communications application further comprises machine-readable instructions to locate a position of the optical sensor on the display, and wherein the transmission spot is centered upon the located position.

A method designated BD including the method designated BC wherein the transmission spot is sized smaller than 5 centimeters diameter.

A method designated BE including the method designated BD wherein the transmission spot is located on a display screen sized greater than 16 centimeters in at least one axis.

A method designated BDA including the method designated BD or BE wherein the instructions to locate a position of the optical sensor on the display include instructions adapted to present at least one gradient in at least one axis on the display.

A method designated BF including the method designated B, BA, BB, BC, BD, BDA or BE wherein the firmware comprises machine-readable instructions for performing a correlation to ensure accurate transmission of the optical digital message.

A method designated BG including the method designated B, BA, BB, BC, BD, BDA, BE, or BF wherein the optical digital message comprises a public key of a cipher.

Changes may be made in the above methods and systems without departing from the scope hereof. It should thus be noted that the matter contained in the above description or shown in the accompanying drawings should be interpreted as illustrative and not in a limiting sense. The following claims are intended to cover generic and specific features described herein, as well as all statements of the scope of the present methods and systems, which, as a matter of language, may be said to fall therebetween.

What is claimed is:

1. A system comprising:
   a first electronic device comprising:
      an optical sensor,
      a digital radio wireless transceiver, and
      a first processor coupled to a first memory, the optical sensor, and the digital radio wireless transceiver, the first memory containing a firmware;
   a computerized device comprising:
      a display subsystem,
      a second digital radio wireless transceiver, and
      a second processor coupled to a second memory, the display subsystem, and the second digital radio wireless transceiver, the second memory containing an optical communications application;
   the optical communications application comprising machine-readable instructions configured to present an optical digital message as a sequence of symbols, each symbol encoded as an intensity selected from a plurality greater than two of intensity levels and each symbol corresponding to a plurality of bits of the optical digital message, at a transmission spot on a screen of the display sub system;
   the firmware comprising machine-readable instructions for receiving the digital message through the optical sensor, the optical digital message comprising at least one of an encryption subkey and an authentication code adapted for authenticating a wireless connection between the first electronic device and the computerized device, and to use the authentication code or encryption subkey of the optical digital message to establish an encrypted wireless connection from the first processor through the digital wireless radio transceiver and the second digital wireless radio transceiver to the second processor.

2. The system of claim 1 wherein the digital message is encoded with at least 3 bits per symbol.

3. The system of claim 2 wherein the intensity of the transmission spot returns to zero between symbols while transmitting the digital message.

4. The system of claim 1 wherein the optical communications application further comprises machine-readable instructions configured to locate a position of the optical sensor on the display, wherein the transmission spot is centered upon the located position, and wherein the transmission spot is surrounded by optical masking patterns.

5. The system of claim 4 wherein the transmission spot is sized smaller than 5 centimeters diameter.

6. The system of claim 5 wherein the display has a screen size exceeding 16 centimeters in at least one axis.

7. The system of claim 5 wherein the display has a screen size exceeding 40 centimeters in at least one axis.

8. The system of claim 4 wherein the machine-readable instructions configured to locate a position of the optical sensor on the display comprise instructions for presenting at least one gradient pattern in at least one axis on the display.

9. The system of claim 1 wherein the firmware comprises machine-readable instructions for performing a correlation to ensure accurate transmission of the optical digital message.

10. The system of claim 1 wherein the optical digital message comprises a public key of a cipher.

11. The system of claim 10 wherein the memory of the computerized device comprises machine-readable instructions for receiving information from the first electronic device and for displaying the information on the display.

12. A method using an intensity-modulated brightness channel to communicate a digital message from a computerized device to a portable electronic device,
providing a computerized device comprising:
a display subsystem,
a first digital radio wireless transceiver, and
a first processor coupled to a first memory, the display subsystem, and the first digital radio wireless transceiver, the first memory containing an optical communications application;
providing a portable electronic device comprising:
an optical sensor,
a second digital radio wireless transceiver, and
a second processor coupled to a second memory, the optical sensor, and the second digital radio wireless transceiver, the second memory containing a firmware;
establishing a radio digital communication channel between the first and second digital radio wireless transceivers;
using the display subsystem of the computerized device and the optical sensor of the portable electronic device to form an optical digital communication channel configured to communicate a plurality of bits of an optical message with intensity modulation of each symbol transmitted by the display system of the computerized device;
sending cryptographic information from the computerized device to the portable electronic device over the optical digital communication channel to allow the portable electronic device to verify cryptographic information sent by the computerized device over the radio communication channel to the portable electronic device and to adopt a session key for encrypting the radio communication channel; and
establishing an encrypted communications session using the radio communication channel, in a manner that ensures the intended portable electronic device is connected to the intended computerized device.

13. The system of claim 1 wherein the firmware further comprises machine readable instructions for performing a correlation to match the authentication code or encryption subkey of the optical digital message with authentication received through the digital wireless transceiver.

14. The method of claim 12 wherein the digital message is encoded with at least 3 bits per symbol.

15. The method of claim 14 wherein the intensity of the transmission spot returns to zero between symbols while transmitting the digital message.

16. The method of claim 12 further comprising locating a position of the optical sensor on the display, and centering the transmission spot upon the located position, and surrounding the transmission spot by masking patterns.

17. The method of claim 16 wherein the transmissions spot is sized smaller than 5 centimeters diameter.

18. The method of claim 16 wherein the instructions to locate a position of the optical sensor on the display include instructions adapted to present at least one gradient in at least one axis on the display.

19. The method of claim 12 wherein the firmware comprises machine-readable instructions for performing a correlation to ensure accurate transmission of the optical digital message.

20. The system of claim 12 wherein the optical digital message comprises at least a portion of a public key of a cipher.

* * * * *